United States Patent [19]
Hirose et al.

[11] Patent Number: 5,985,542
[45] Date of Patent: Nov. 16, 1999

[54] DIAGNOSTIC KIT

[75] Inventors: Masao Hirose; Masaki Mori, both of Aichi; Koichiro Komai; Koichi Saito, both of Hyogo, all of Japan

[73] Assignee: Sumitomo Chemical Company, Limited, Osaka, Japan

[21] Appl. No.: 08/859,098

[22] Filed: May 20, 1997

[30] Foreign Application Priority Data

May 20, 1996 [JP] Japan .................................. 8-124461

[51] Int. Cl.$^6$ ........................... C12Q 1/70; G01N 33/53; G01N 33/573; A61K 39/395
[52] U.S. Cl. ................................ 435/5; 435/7.1; 435/7.4; 435/7.92; 435/960; 435/975; 424/130.1; 424/146.1
[58] Field of Search .................................. 435/5, 7.1, 7.4, 435/7.92, 960, 975; 424/130.1, 146.1

[56] References Cited

U.S. PATENT DOCUMENTS 5,830,667 11/1998 Alvarez ..................................... 435/7.1

FOREIGN PATENT DOCUMENTS

| | | |
|---|---|---|
| 02234062 | 9/1990 | Japan . |
| 2234062 | 9/1990 | Japan . |
| 665299 | 3/1994 | Japan . |
| 827193 | 1/1996 | Japan . |
| 827194 | 1/1996 | Japan . |
| 827195 | 1/1996 | Japan . |
| 827196 | 1/1996 | Japan . |
| 827197 | 1/1996 | Japan . |
| 827198 | 1/1996 | Japan . |
| 827199 | 1/1996 | Japan . |
| 8143599 | 6/1996 | Japan . |
| 92/22656A1 | 12/1992 | WIPO . |
| WO9719112 | 5/1997 | WIPO . |

OTHER PUBLICATIONS

George et al., *Pre–Translational Regulation of Cytochrome P450 Genes is Responsible for Disease*, etc., XP–002058405, Storr Liver Unit. Dept. of Gastroenterology and Hepatology, University of Sydney (Nov., 1994).
Belloc et al. 1996 Toxicology 106 pp. 207–219, Feb. 1996.
Kirby et al. 1996 Toxicologic PAthology 24(4) pp. 458–467, Aug. 1996.
Wang et al. 1996 Drug MEtabolism and Disposition 24(7) pp. 786–791 Sep. 1996.
Toru et al. 1997 Kanzo (Acta Hepatologica Japonica) 38 (4) pp. 258–259 Abstract only, Apr. 1997.
WPI Abstract Accession No. 96–136339/199614 & JP 080027198 A.
WPI Abstract Accession No. 96–136337/199614 & JP 080027196 A.
WPI Abstract Accession No. 96–136335/199614 & JP 080027194 A.
Sigma Chemical Company, "Biochemicals organic compounds for research and diagnostic agents", published 1993, Sigma Chemical Company, pp. 2215 and 2222.

*Primary Examiner*—Michael P. Woodward
*Assistant Examiner*—Mary K Zeman
*Attorney, Agent, or Firm*—Birch, Stewart, Kolasch & Birch, LLP

[57] ABSTRACT

The present invention provides:

a diagnostic kit for liver diseases such as hepatitis C and alcoholic cirrhosis to be applied to a human serum sample, which contains an antibody capable of recognizing a human cytochrome P450; and a process for determining the concentration of a cytochrome P450 in a human serum for diagnosis of hepatitis C and alcoholic cirrhosis.

6 Claims, 4 Drawing Sheets

(a)P450 1A2

(b)P450 2C8

DIAGNOSTIC KIT

BACKGROUND OF THE INVENTION

1. Field of the Invention

The present invention relates to a diagnostic kit for hepatitis C and alcoholic cirrhosis.

2. Description of the Prior Art

Activities of enzymes such as GOT (glutamic-oxaloacetic transaminase), GPT (glutamic-pyruvic transaminase), γ-GTP (γ-glutamyl transpeptidase) and the like have been measured as biological markers of human liver complaints with certain kits for diagnosis.

These enzyme activities, however, were not always satisfactory to specify a disease, since they did not distinguish liver diseases, such as viral hepatitides hepatitis A, hepatitis B, non-A non-B hepatitise, alcohol-induced hepatic injury and drug-induced hepatic injury.

Hence a further marker to specify certain liver diseases or a kit therefor have been desired.

SUMMARY OF THE INVENTION

The present inventors have found that the concentration of a human cytochrome P450, a specific enzyme which is not usually present in human blood, extremely increases in sera when the subject is suffering from a liver disease such as hepatitis C and alcoholic cirrhosis and that a novel and useful kit for determining the concentration of the enzyme enables the diagnosis of said liver diseases.

Thus the present invention provides:

1. a diagnostic kit (hereinafter, referred to as the diagnostic kit of the invention) for hepatitis C and alcoholic cirrhosis to be applied to a human serum sample, which comprises an antibody capable of recognizing a human cytochrome P450;
2. a diagnostic kit for hepatitis C and alcoholic cirrhosis to be applied to a human serum sample, which comprises:
   (a) a solid support to which an antibody capable of recognizing a human cytochrome P450 is bound, and
   (b) a reagent containing a labeled antibody capable of recognizing a human cytochrome P450; and
3. a process (hereinafter, referred to as the process of the invention) for determining the concentration of a human cytochrome P450 in human serum for diagnosis of hepatitis C and alcoholic cirrhosis, which comprises:
   (a) conducting an antigen-antibody reaction by adding a human serum sample to a solid support to which an antibody capable of recognizing a human cytochrome P450 is bound, then removing excess human cytochrome P450 and unreacted matters by washing,
   (b) conducting an antigen-antibody reaction by adding a labeled antibody capable of recognizing a human cytochrome P450 to the reaction product, then removing excess labeled antibody capable of recognizing a human cytochrome P450 by washing, and
   (c) then detecting said cytochrome P450 by means of the label on said labeled antibody in the reaction product.

It can be understood that the antibodies capable of recognizing the P450 subfamilies 1A2, 2C8, 2E1 and 3A4 subfamilies, respectively, reacted with the corresponding subfamilies and allowed determination of the concentration of cytochrome P450 with specificity to each of the subfamilies and quantitatively.

FIGS. 2A–2D

Patient 1: suffering from alcoholic cirrhosis,

Patient 2: suffering from hepatitis C,

Patient 3: suffering from non-alcoholic cirrhosis, and

Patient 4: suffering from primary biliary cirrhosis.

Figure 2A:
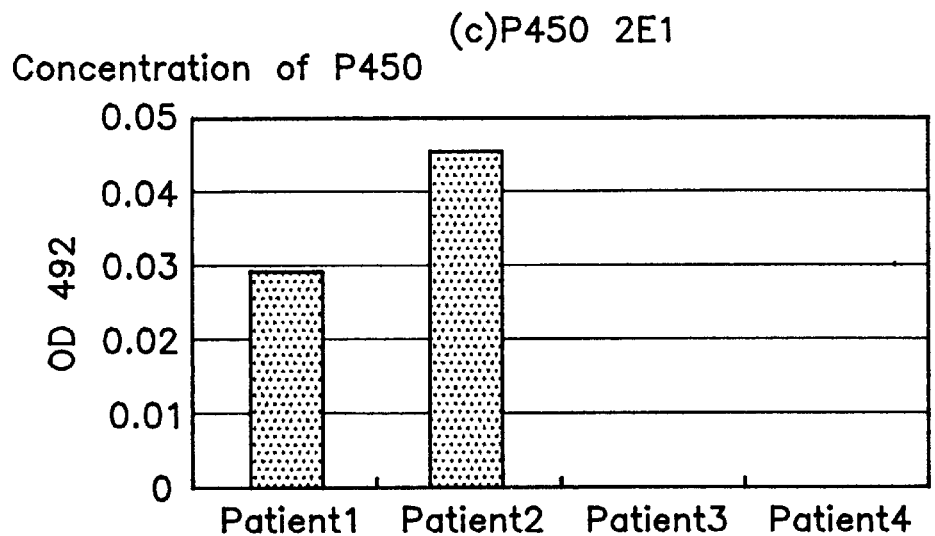
Figure 2B:
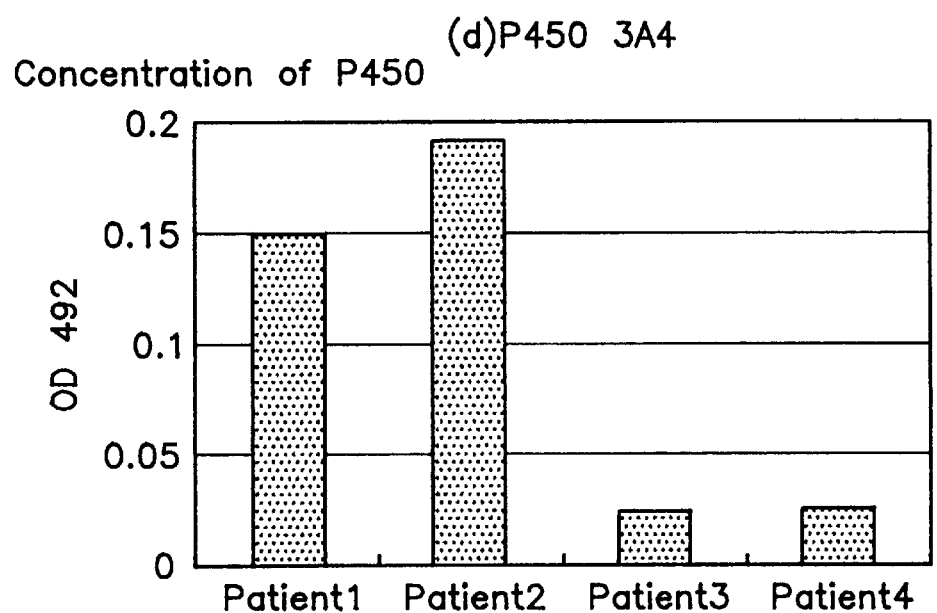
Figure 2C:
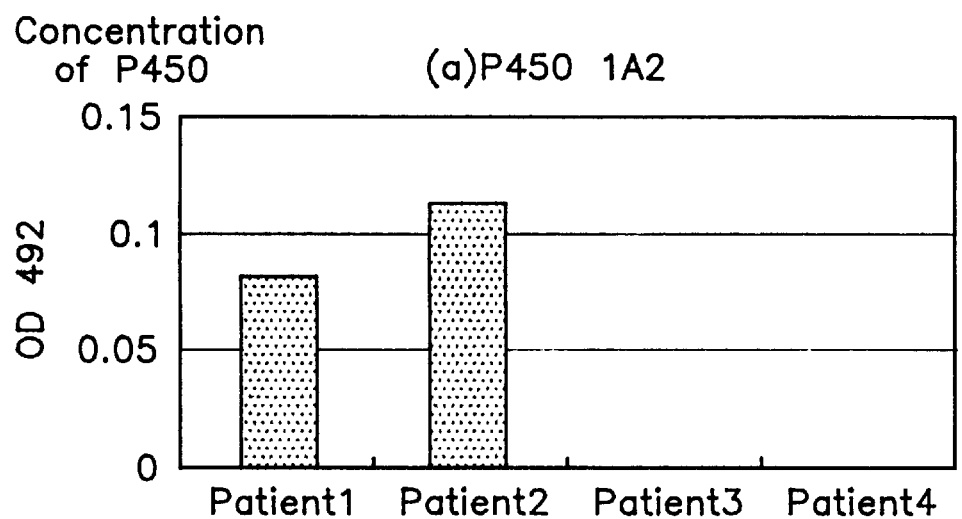
Figure 2D:
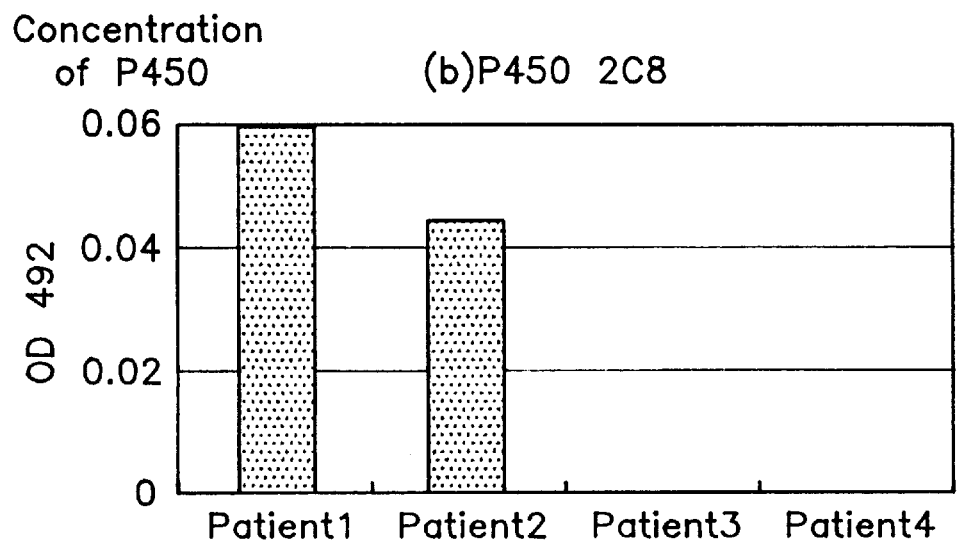

FIGS. 2A–2D shows the results of determination of the concentration of cytochrome P450 in the sera sample of patients with various liver diseases, using the diagnostic kit of the present invention.

It has been revealed that the concentrations of cytochrome P450 in the sera of patients with liver diseases such as hepatitis C and alcoholic cirrhosis have extremely increased.

DESCRIPTION OF THE PREFERRED EMBODIMENTS

First, description will be made to the first aspect of the invention relating to a diagnostic kit for hepatitis C and alcoholic cirrhosis to be applied to a human serum sample, which comprises an antibody capable of recognizing a human cytochrome P450.

The antibody that can recognize human P450 can be used in the present invention and includes, for example, antibodies capable of recognizing P450 subfamilies such as 1A1, 1A2, 2B6, 2C8, 2C9, 2C18, 2C19, 2D6, 2E1 or 3A4.

Preferred antibodies are those having substantially no cross-reactivity to other human cytochrome P450 subfamilies than a specific human cytochrome P450 subfamily. In other words, such antibodies have a strict reaction specificity to 1A1/2, 2C8/9/18, 2E1 or 3A4, or they are capable of substantially distinguishing 1A1/2, 2C8/9/18, 2E1 or 3A4 respectively.

The means for obtaining such antibody is not limited, but as an antigen for immunizing a mammalian animal, human cytochrome P450 which is substantially uncontaminated with other human cytochrome P450 subfamilies than the specific human cytochrome P450 subfamily is usually used.

While human cytochrome P450 can be purified from a human liver, the obtained human cytochrome P450 can not always be free from slight contamination by similar cytochrome P450 subfamilies and can not be purified to a state of single component without extreme difficulty.

Particularly, in the case of a cytochrome P450 subfamily which contributes to a metabolism of the important pharmacological molecule despite its low content, it is almost impossible to obtain the cytochrome P450 in a state of single component by purification.

When such material is used as the antigen, an antibody which has substantially no cross-reactivity to other human cytochrome P450 subfamilies than the specific human cytochrome P450 subfamily can not be prepared.

Further, if it is at all possible to obtain a human cytochrome P450 in a state of single component by purification, the yield may be too little to sufficiently immunize a mammalian animal or only a very low antibody titer can be attained. Moreover, obtaining of a great number of human livers is almost impossible from ethical and technical viewpoints and is not practical.

Therefore, it is preferred to prepare the antigen for immunization of a mammalian animal by a process including extraction and purification from a transformant yeast obtained by recombinant DNA technology expressing only a specific cytochrome P450 subfamily.

More specifically, the process for producing the antigen comprises:
(1) cloning a gene encoding a human cytochrome P450 subfamily,
(2) constructing an expression plasmid for expressing the cloned gene in yeast,
(3) introducing the constructed yeast expression plasmid into yeast to produce recombinant yeast expressing the human cytochrome P450 subfamily,
(4) culturing the obtained recombinant yeast, disrupting them, preparing a yeast microsome fraction,
(5) solubilizing said fraction using a surfactant or the like, purifying the obtained solubilized supernatant by appropriate column chromatography such as octylaminocephalose column chromatography, anion exchange column chromatography, hydroxyapatite column chromatography, or the like,
(6) immunizing a mammalian animal with the purified human P450 subfamilies as the antigen, and
(7) collecting blood from the mammalian animal, and then isolating and purifying the antibody from the obtained blood.

The nucleotide sequence of the "gene encoding a human cytochrome P450 subfamilies" is described in references and the gene encoding a human cytochrome P450 subfamily can be isolated from the commercially available cDNA library derived from human liver cells by means of a conventional process including PCR and the like.

The promoter for expressing the gene encoding a human cytochrome P450 subfamily in yeast may be any promoter used in the conventional yeast expression system and is not particularly limited but includes, for example, yeast alcohol dehydrogenase gene promoter (hereinafter, abbreviated as ADH promoter), glyceraldehyde triphosphate dehydrogenase gene promoter (hereinafter, abbreviated as GAPDH promoter), phosphoglycerate kinase gene promoter (hereinafter, abbreviated as PGK promoter) and the like.

ADH promoter can be prepared, for example, from yeast expression vector pAAH5 (available from Washington Research Foundation; see Ammerer et al, Method in Enzymology, 101 (p. 192–201)) carrying yeast ADH1 promoter and terminator by means of the usual gene manipulation process. The yeast ADH1 promoter is covered by U.S. Pat. No. 299,733 of Washington Research Foundation and a license from the patentee is necessary for industrial or commercial utilization thereof in the United States.

The promoter for expression in yeast described above and the yeast expression plasmid carrying the gene containing a nucleotide sequence encoding the human cytochrome P450 subfamily can be constructed by a conventional gene recombining process.

Said process includes, for example, a process in which a cDNA encoding the human cytochrome P450 subfamilies is inserted into a Hind III site of the yeast expression vector pAAH5N, described in JP-A-2-211880, carrying ADH promoter and terminator or the like.

The recombinant yeast expressing the human cytochrome P450 subfamily can be obtained by introducing the constructed yeast expression plasmid into a yeast by a conventional process, for example, the protoplast process.

Strains of the yeast to be used in the present invention includes, for example, *Saccharomyces cerevisiae* and the like. Preferred strains include *Saccharomiyces cerevisiae* AH 22 (ATCC 38626).

Extraction and purification of cytochrome P450 subfamilies from the recombinant yeast can be conducted by a usual process such as one described in, for example, J. Biochem., Vol. 98, No. 1, p 167–175 (1985) and the like.

Specifically, the obtained recombinant yeast is cultured and the yeast mass is sonicated after converting to spheroplast by lysis enzyme or the like.

A yeast microsome fraction is prepared by centrifugation and, after solubilizing said fraction with a surfactant and sodium cholate and so on (together with precipitation by ammonium sulfate, polyethylene glycol or the like, if necessary), the obtained solubilized supernatant is purified by any kind of column chromatography which may be octylaminocephalose column chromatography, anion exchange column chromatography, hydroxyapatite column chromatography, or the like. A preferred apparatus for isolation and purification is the high performance liquid chromatography.

Preparation of the antibody to be used in the present invention can be carried out, for example, by immunizing a mammalian animal with the human P450 subfamilies purified in this manner as the antigen, collecting blood from the mammalian animal, and then isolating and purifying the antibody from the obtained blood.

The immunization of mammalian animals such as mouse, hamster, guinea-pig, chicken, rat, rabbit, dog and the like is effected, for example, by one or more administration of the antigen according to the general immunizing method proposed by W. H. Newsome et al described in J. Assoc. Off. Anal. Chem., 70(6), 1025–1027 (1987).

Preferably, the administration occurs twice or thrice at intervals of 7 to 30 days, particularly at 12 to 16 days.

A standard amount for administration is, for example, about 0.05 to about 2 mg of the antigen per administration. The route of administration may be selected from subcutaneous, intracutaneous, intraperitoneal, intravenous, intramuscular administrations and others. Preferred manner of administration is injection which may be intravenous, intraperitoneal or subcutaneous.

More preferred manner is a combination of subcutaneous injection and intraperitoneal injection. In this case, the antigen is used in the form of a solution in an appropriate buffer, for example, a sodium phosphate buffer, physiological saline or the like which contains a conventional adjuvant such as Freund's complete adjuvant (a mixture of Aracel A, Bayol F and killed tubercle bacillus), RAS [MPL (Monophosphoryl Lipid A)+TDM (Synthetic Trehalose Dicorynomycolate)+CWS (Cell Wall Skeleton) adjuvant system], aluminum hydroxide and the like, but depending on the route of administration, condition or the like, the above adjuvant may be omitted.

The adjuvant to be used herein refers to a substance which enhances non-specifically the immunization reaction of an antigen when administered together with the antigen.

After 0.5 to 4 months of breeding of the above mammalian animal without treatment, a small amount of a serum sample of the animal is withdrawn through an auricular vein and assayed for antibody titer.

When the antibody titer increases, the administration of the antigen is repeated an appropriate number of times depending on the circumstances. For example, additional one administration is given in a dose of 100 μg to 1,000 μg, particularly of 50 μg to 500 μg, of the antigen.

After 1 to 2 months from the last administration, blood is collected from the immunized mammalian animal according to the usual method, and the antibody of the present invention is obtained in the form of a polyclonal antiserum by treating said serum with conventional means, for example, centrifugation, precipitation with ammonium sulfate or polyethylene glycol, chromatography including gel filtration chromatography, ion exchange chromatography, affinity chromatography, or the like.

The serum may be treated, for example, at 56° C. for 30 minutes to inactivate the complements.

The antibodies which have substantially no cross-reactivity to other human cytochrome P450 subfamilies than a specific human cytochrome P450 subfamily and which have a high specificity and affinity can be prepared by isolating immunocompetent B cells from the above immunized mammalian animal, fusing the immunocompetent B cells with malignant cells which are permanently fissionable, isolating the resulting fusion cells, selecting and cloning hybridoma cells capable of producing the desired antibody, and culturing said hybridoma cells in vitro or in vivo in order to produce the monoclonal antibody.

As used herein, "no cross-reactivity to other human cytochrome P450 subfamilies than a specific human cytochrome P450 subfamily" means that a selective recognition in which the cross-reactivity to other human cytochrome P450 subfamily than a specific human cytochrome P450 subfamilies is less than about ¼, preferably less than about ¹⁄₂₀, and more preferably less than ¹⁄₁₀₀, is substantially possible.

The degree of the cross-reactivity is given by 1/C, wherein the substrate protein concentration at which a specific human cytochrome P450 subfamily can be detected by the immunoblotting method is taken as 1 and the concentration of other human cytochrome subfamilies detected by the same method is C.

Next description will be made to the second aspect of the present invention relating to the diagnostic kit for hepatitis C and alcoholic cirrhosis, which comprises:

(a) a solid support to which an antibody (the first antibody) capable of recognizing a human cytochrome P450 is bound, and (b) a reagent containing a labeled antibody (the second antibody) capable of recognizing a human cytochrome P450.

In this aspect of the invention, the antibody (the first antibody) to be used may not be specifically limited and an antibody that can recognize human cytochrome P450 can be used.

The antibody (the first antibody) includes, for example, antibodies capable of recognizing P450 subfamilies selected from a group consisting of 1A1, 1A2, 2B6, 2C8, 2C9, 2C18, 2C19, 2D6, 2E1 or 3A4.

Preferred antibody are those having substantially no cross-reactivity to other human cytochrome P450 subfamilies than a specific human cytochrome P450 subfamily as described above.

The kit may further comprise:

(c) a standard solution of human cytochrome P450, (d) a buffer, (e) a polypeptide for inhibiting non-specific adsorption and formation of aggregate, and optionally an additive such as surfactant and (f) a pipette, a reaction vessel, a calibration curve and so on.

The solid support may take various designs and shapes depending on specific purpose desired on use. For example, it may be in a form of a dish, sphere, plate, small rod, cell, small bottle, small tube, fiber, network or the like.

Specific examples to be used include a microtiter plate made of transparent plastic material such as polyvinyl chloride or polystyrene, small sphere, tube, rod or the like made of polystyrene and polystyrene latex.

For binding an antibody (the first antibody) capable of recognizing a human cytochrome P450 on such solid support, for example, the solid support is usually activated previously by a conventional method using glutaraldehyde, bromocyan or the like.

Usable antibody binding solution includes, for example, about 10 mM phosphate buffer (pH=7.4) containing 140 mM sodium chloride or the like. The antibody binding solutions preferably contains, for example, an antibody at a concentration of about 0.05 µg/ml to about 1 µg/ml.

The treatment period may be, for example, about 6 hours to about 24 hours. In a specific example in the specification, 96-well microtiter plate made of polystyrene can be used.

The antibody (the first antibody) capable of recognizing a human cytochrome P450 may be indirectly or directly bound on such solid support.

When an antibody (the first antibody) capable of recognizing a human cytochrome P450 is bound indirectly on such solid support, it is preferred to bind the antibody (the first antibody) capable of recognizing a human cytochrome P450 on the support through an intervening spacer and/or high molecular weight carrier molecule which is not recognized by the antibody. The high molecular weight carrier molecule which is not recognized by the first antibody means the high molecular weight carrier molecule which is not used in the preparation of the antibody. This is usually used when the first antibody is polyclonal.

The labeled antibody (the second antibody) of the antibody (the first antibody) capable of recognizing a human cytochrome P450 can be obtained by labeling with an enzyme such as peroxidase, alkaline phosphatase, β-D-galactosidase, glucose oxidase, glucoamylase, carbonic anhydrase, acetylcholine esterase, lysozyme, maleate dehydrogenase, glucose-6-phosphate dehydrogenase and the like.

In this case, after incubating and removing the second antibody in a free state by washing, the second antibody can be detected by measuring the color development accompanying the reaction of said labeling enzyme with a substrate thereof. For example, when peroxidase is used as the label, brown or yellow color is developed by combining hydrogen peroxide as the substrate and diaminobenzidine or o-phenylenediamine as the developing reagent.

When glucose oxidase is used as the label, the substrate may be, for example, 2,2'-azino-di-(3-ethylbenzothiazolin-6-sulfonate) (ABTS).

The antibody (the first antibody) capable of recognizing a human cytochrome P450 can also be labeled with biotin using, for example, "protein biotinylation system" manufactured by Amersham. In this case, after incubating and removing the second antibody in a free state by washing, the second antibody can be detected with high sensitivity by measuring the color development accompanying the reaction upon treatment of the second antibody for binding with an enzyme, for example, peroxidase, alkaline phosphatase, β-D-galactosidase, glucose oxidase, glucoamylase, carbonic anhydrase, acetylcholine esterase, lysozyme, maleate dehydrogenase, glucose- 6-phosphate dehydrogenase and the like, labelled with a substance (streptavidin) which binds specifically to biotin.

The process for determining the concentration of a cytochrome P450 in human serum for diagnosis of hepatitis C and alcoholic cirrhosis will be described in further detail as below.

The process comprises:

(1) conducting an antigen-antibody reaction by adding a human serum sample to a solid support to which an antibody (the first antibody) capable of recognizing a human cytochrome P450 is bound, then removing excess human cytochrome P450 and unreacted matters by washing, (2) conducting an antigen-antibody reaction by adding a labeled antibody (the second antibody) capable of recognizing a human cytochrome P450 to the reaction product, then removing excess labeled antibody (the second antibody) capable of recognizing a human cytochrome P450 by washing, and (3) then detecting said cytochrome P450 by means of the label on said labeled antibody (the second antibody) in the reaction product.

For example, the antibody (the first antibody) capable of recognizing a human cytochrome P450 purified as described above is placed in a 96-well microtiter plate such as Nunc-Immuno Plate MaxiSorp (Trademark) available from Nunc such that the amount of protein is 50 ng to 500 ng, preferably 200 ng to 400 ng/well and allowed to stand at about 4° C. to room temperature for about 2 hours to about 20 hours.

Then, wells are washed two to five times with about 100 µl to about 500 µl of about 10 mM phosphate buffer (pH=7.4) containing about 140 mM sodium chloride and about 0.1% Tween 20. Further, about 100 µl to about 500 µl of about 10 mM phosphate buffer (pH=7.4) containing about 140 mM sodium chloride and about 1% bovine serum albumin is added to the wells for the purpose of blocking and allowed to stand at about 4° C. to room temperature for about 30 minutes to 60 minutes.

Then, wells are washed two to five times with about 100 µl to about 500 µl of about 10 mM phosphate buffer (pH=7.4) containing about 140 mM sodium chloride and about 0.1% Tween 20.

To a solid support treated in this manner is added a human serum as the sample which is prepared by diluting a serum with distilled water, a buffer, physiological saline or the like if necessary (the serum being obtained, for example, as a supernatant formed by centrifuging about 1 ml to about 10 ml of withdrawn blood as the sample at about 4° C. and 2,000 G for 15 minutes to remove precipitates) in an amount of about 50 µl to about 200 µl per well and allowed to stand at room temperature for 1 hour to 2 hours to effect antigen-antibody reaction.

Then, wells are washed two to five times with about 100 µl to about 500 µl of about 10 mM phosphate buffer (pH=7.4) containing about 140 mM sodium chloride and about 0.1% Tween 20.

Next, the reaction product is treated, for example, with about 50 µl to about 200 µl, preferably about 100 µl, of a solution of a labeled antibody prepared by diluting a biotin-labeled antibody (the second antibody) capable of recognizing human cytochrome P450 about 250 to 2,000 times, preferably 500 times, with about 10 mM buffer (pH=7.4) (about5 mM to about50 mM) containing about 140 mM sodium chloride and about 0.1% Tween 20 and allowed to stand at room temperature for 1 hour to 2 hours to effect antigen-antibody reaction.

Then, wells are washed two to five times with about 100 µl to about 500 µl of about 10 mM phosphate buffer (pH=7.4) containing about 140 mM sodium chloride and about 0.1% Tween 20 in order to remove the excess labeled antibody (the second antibody) capable of recognizing human cytochrome P450.

Next, the reaction product is treated with about 50 µl to about 200 µl preferably about 100 µl of streptavidin-labeled horse-radish peroxidase (HRP, for example, commercially available from Amersham), allowed to stand at about 4° C. to room temperature for about 30 minutes to 60 minutes, washed in a similar manner to that described above, treated with a substrate solution (for example, 4 mM o-phenylenediamine, 0.004% hydrogen peroxide, 0.02 M citrate, 0.05 M Na$_2$HPO$_4$/pH 5.0) and allowed to stand at room temperature for about 10 minutes to about 60 minutes to develop brown color depending on the amount of the antigen (i.e. human cytochrome P450).

For diagnosis of hepatitis C and alcoholic cirrhosis, the concentration of cytochrome P450 in the human serum can be determined by measuring absorbance of the well at a substrate-specific wave length (for example, 492 nm for o-phenylenediamine) with a spectrophotometer such as a microplate-reader for 96-well microtiter plate or the like.

For determination of the concentration, it is convenient to prepare a calibration curve previously using standard solutions of the human cytochrome P450.

In the diagnostic kit of the present invention, those utilizing other principles, such as for example, immunoblotting method, ELISA method (see: "Current Protocols in Molecular Biology", Wiley Interscience (1991)) and the like, than that described above can be employed.

The following Examples illustrate the present invention in detail, however, it should not be construed as a limitation upon the scope thereof.

EXAMPLES

Reference Example 1
Obtaining a Gene having a Nucleotide Sequence Encoding a Human Cytochrome P450

A cDNA encoding a human cytochrome P450 was obtained from a commercially available human liver-derived cDNA library (Clontech) by PCR process using a cloning primer designed on the basis of the known nucleotide sequence of human cytochrome P450 gene.

Reference Example 2
Construction of a Yeast Expression Plasmid.

A protein coding region of a human cytochrome P450 gene was amplified by PCR process using a cloning primer. The obtained fragment was inserted into a pUCA vector (a plasmid for subcloning prepared by altering Eco RI site of pUC19 to Hind III site and changing the cloning site between the formed Hind III and Hind III to the following cloning site:

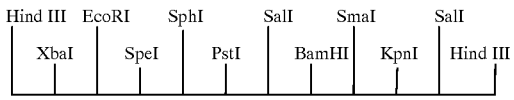

cutting off with Hind III and inserting into pAAH5N to construct a yeast expression plasmid for human cytochrome P450.

Reference Example 3
Preparation of Transformed Yeast Cells

Sacchromyces cerevisiae AH 22 was inoculated in YPD medium (1% yeast extract, 2% polypeptone and 2% glucose) and the culture was shaken at 30° C. for 18 hours. Then, cells were harvested by centrifugation (5,000×g, 10 minutes).

The obtained cells were suspended in 0.2 M LiCl solution and the suspension was centrifuged (500×g, 10 minutes) again. The obtained pellets were added to 20 µl of 1 M LiCl solution, 30 µl of 70% polyethylene glycol 4000 solution and 10 µl of a solution containing about 1.0 µg of the yeast expression plasmid for human cytochrome P450.

They were sufficiently mixed, incubated at 30° C. for 1hour, and mixed with 140 µl of sterile water under stirring.

The obtained solution was spread on a SD synthetic medium plate (2.0% glucose, 0.67% amino acids free nitrogen source (Nitrogen base w/o amino acids, manufactured by Difco), 20 μg/ml histidine and 2.0% agar) and incubated at 30° C. for 3 days to select transformed yeast cells carrying the above described yeast expression plasmid.

Reference Example 4
Measurement of Human Cytochrome P450 Expressed in Yeast

Cells were harvested from 200 ml of the cultivation solution (SD synthetic medium, density of cells: about $1.5 \times 10^7$ cells/ml) containing the transformed yeast cells capable of expressing the human cytochrome P450 in yeast prepared in Reference Example 3.

Said cells were suspended in 10 ml of 100 mM potassium phosphate buffer (pH=7.0) and the suspension was centrifuged (5,000×g, 10 minutes). The obtained pellets were suspended in 2.0 ml of fresh 100 mM potassium phosphate buffer (pH=7.0) and the suspension was divided in 1.0 ml portions into two cuvettes. Carbon monoxide was blown into a sample cuvette and 5–10 mg of dithionite was added thereto.

After stirring, difference spectra at 400–500 nm were measured and concentration of the human cytochrome P450 in yeast was calculated. The amount of expressed human cytochrome P450 in the transformed yeast cells was at a level of about $10^5$–$10^6$ molecule/cell.

Reference Example 5
Preparation of a Microsome Fraction from the Transformed Yeast Cells Cells were harvested from 3.8 l of the cultivation solution (SD synthetic medium, density of cells: about $1.0 \times 10^8$ cells/ml) containing the transformed yeast cells capable of expressing the human cytochrome P450 in yeast prepared in Reference Example 3. Said cells were suspended in 400 ml of Buffer A (10 mM Tris-HCl (pH=7.5), 2M sorbitol, 0.1 mM DTT and 0.2 mM EDTA). To the suspension was added 160 mg of Zymolyase (Zymolyase 100T, manufactured by Wako Pure Chemical Ind.) and the mixture was incubated at 30° C. for 60 minutes.

Spheroplasts obtained by centrifugation (5,000×g, 10 minutes) were suspended in Buffer A and centrifuged (5,000×g, 10 minutes) again. After repeating the same centrifugation once again for washing, the spheroplasts were suspended in 200 ml of a buffer (10 mM Tris-HCl (pH=7.5), 0.65 M sorbitol and 0.1 mM DTT) and subjected to sonication (50 W, 5 minutes). The disrupted product was centrifuged (9,000×g, 20 minutes) to collect a supernatant, which was further centrifuged (125,000×g, 70 minutes) to collect precipitates. Collected precipitates were re-suspended in 10 ml of 0.1 mM potassium phosphate buffer (pH=7.4) to give a microsome fraction.

Reference Example 6
Purification of the Human Cytochrome P450 from the Microsome Fraction The microsome fraction (about 300 mg) containing the human cytochrome P450 obtained in Reference Example 5 was diluted with 0.1 M potassium phosphate buffer (pH=7.22, Buffer B) containing 1 mM DTT, 1 mM EDTA, 0.25 mM PMSF and 20% glycerol to 3 mg/ml. To the dilution was added dropwise sodium cholate to the final concentration of 0.6% and allowed to stand at 4° C. for 30 minutes to dissolve the human cytochrome P450.

After centrifuging (200,000×g, 30 minutes) the solution, the supernatant was applied to a column packed with 15 ml of octylaminocephalose 4B (Pharmacia) equilibrated with Buffer B containing 0.5% sodium cholate to bind the human cytochrome P450 on the carrier. The column was washed sufficiently with Buffer B to remove the non-bound matter and the human cytochrome P450 was eluted with a buffer prepared by adding 0.2% polyoxyethylene nonylphenyl ether (manufactured by Kao Corp., trade name: Emulgen 911) to Buffer B. Active fractions were collected and dialyzed overnight against 0.02 M Tris-acetate buffer (pH=7.2, Buffer C) containing 20% glycerol. Then, upon applying the fractions to DEAE-5PW (manufactured by Toso) HPLC column equilibrated with a buffer prepared by adding 0.4% polyoxyethylene nonylphenyl ether (manufactured by Kao Corp., trade name: Emulgen 911) to Buffer C, the human cytochrome P450 was eluted in non-bound fractions.

Subsequently, the fractions were applied to a hydroxyapatite (manufactured by Koken) HPLC column equilibrated with 0.01 M sodium phosphate buffer (pH=7.2, Buffer D) containing 0.2% polyoxyethylene nonylphenyl ether (manufactured by Kao Corp., trade name: Emulgen 911), 0.2% sodium cholate and 20% glycerol. The column was washed sufficiently with Buffer D to remove the non-bound matter and the human cytochrome P450 was eluted with a sodium phosphate of linear concentration gradient.

Subsequently, active fractions were collected and the fractions were applied to a hydroxyapatite (manufactured by Biorad) HPLC column equilibrated with 0.01 M phosphate buffer (pH=7.2, Buffer E) containing 20% glycerol. The column was washed sufficiently with Buffer E and the human cytochrome P450 was eluted with O.35 M sodium phosphate containing 0.05% sodium cholate and 20% glycerol. Active fractions were collected to give purified human cytochrome P450.

Preparation Example 1
Preparation of an Antibody (the first antibody) Capable of Recognizing a Human Cytochrome P450

The purified human cytochrome P450 obtained in Reference Example 6 was dissolved in the physiological saline to a concentration of 1 mg/ml. To 2 ml of the solution was added 40 μl of RAS [MPL (Monophosphoryl Lipid A)+TDM (Synthetic Trehalose Dicorynomycolate)+CWS (Cell Wall Skeleton) adjuvant system] (manufactured by Sigma) previously incubated at 42° C. to 43° C. and they were mixed sufficiently.

The obtained mixture was administered to New Zealand White rabbits (female, 14 weeks old, average 2.4 kg) at a rate of 1 ml per rabbit. Precisely, the mixture was subcutaneously given at 10 dorsal sites at a dose of 100 μl.

After 3 weeks and 5 weeks, the mixture was administered again, using half the amount. During this period, blood samples were collected through auricular veins and assayed for antibody titer. Since the antibody titer increased after the second booster, immunized rabbits were bled to death through their caroid arteries. The obtained blood was placed in a Separapit tube (manufactured by Sekisui Chemical), incubated at 37° C. for 2 hours, centrifuged (3,000 rpm, 20 minutes, room temperature) and the supernatant was recovered to give an antiserum. The obtained antiserum was treated at 56° C. for 30 minutes to inactivate the complements.

Then, after adding 10 mM phosphate buffer (pH=7.4) containing 140 mM sodium chloride and 0.1% Tween 20 and 1 ml of saturated ammonium sulfate to 1 ml of the antiserum, the mixture was stirred for 30 minutes and centrifuged at 4° C. and 10,000 rpm for 10 minutes to separate precipitates. To the obtained precipitates were added 1 ml of PBS and 1 ml of saturated ammonium sulfate.

The mixture was stirred for 30 minutes and centrifuged again at 4° C. and 10,000 rpm for 10 minutes to separate precipitates. The obtained precipitates were dissolved in 1 ml of 10 mM phosphate buffer (pH=7.4) containing 140 mM sodium chloride and 0.1% Tween 20 and 1 ml of saturated ammonium sulfate and dialyzed overnight against 1 liter of PBS in order to remove ammonium sulfate to give an IgG fraction, which was used as the (first) antibody in the following test.

Preparation Example 2
Preparation of a Labeled Antibody (the second antibody) Capable of Recognizing a Human Cytochrome P450

A labeled antibody (the second antibody) capable of recognizing a human cytochrome P450 was obtained by biotin-labeling the (first) antibody obtained in Preparation Example 1 with a protein-biotinylation system available from Amersham.

Preparation Example 3
Preparation of a Solid Support to which an Antibody Capable of Recognizing a Human Cytochrome P450 is Bound The antibody (the first antibody) capable of recognizing a human cytochrome P450 prepared in Preparation Example 1 was placed in a 96-well microtiter plate [Nunc-Immuno Plate MaxiSorp (Trademark), manufactured by Nunc] such that the amount of protein is 250 ng/well and allowed to stand at 4° C. for 16 hours.

Then, wells were washed three times with 200 µl of 10 mM phosphate buffer (pH=7.4) containing 140 mM sodium chloride and 0.1% Tween 20. Further, 150 µl of 10 mM phosphate buffer (pH=7.4) containing 140 mM sodium chloride and 1% bovine serum albumin was added to the wells for blocking purpose and allowed to stand at room temperature for 60 minutes.

Then, wells were washed three times with 200 µl of about 10 mM phosphate buffer (pH=7.4) containing 140 mM sodium chloride and 0.1% Tween 20 to obtain the desired solid support.

Test Example 1
Determination of the Concentration of a Cytochrome P450 in a Human Serum for Diagnosis of Hepatitis C and Alcoholic Cirrhosis (part 1)

To a solid support obtained in Preparation Example 3 was added 100 µl per well of standardized human cytochrome P450 solutions (adjusted to 5, 2.5, 1.25, 0.625, 0.3125 and 0.16 pmol P450/ml) and allowed to stand at room temperature for 1 hour to effect antigen-antibody reaction.

Next, the reaction product was treated with 100 µl of a solution of a labeled antibody prepared in Preparation Example 3 by diluting a biotin-labeled antibody (the second antibody) capable of recognizing human cytochrome P450 500 times with 10 mM phosphate buffer (pH=7.4) containing 140 mM sodium chloride and 0.1% Tween 20 and allowed to stand at room temperature for 1 hour to effect antigen-antibody reaction.

Then, wells were washed three times with about 200 µl of 10 mM phosphate buffer (pH=7.4) containing 140 mM sodium chloride and 0.1% Tween 20 in order to remove the excess labeled antibody (the second antibody) capable of recognizing human cytochrome P450.

Next, the reaction product was treated with 100 µl of streptavidin-labeled horse-radish peroxidase (HRP, for example, commercially available from Amersham), allowed to stand at room temperature for 30 minutes, washed in a manner similar to that described above, treated with a substrate solution (4 mM o-phenylenediamine, 0.004% hydrogen peroxide, 0.02 M citrate, 0.05 M $Na_2HPO_4$/pH 5.0) and allowed to stand at room temperature for 30 minutes to develop brown color reflecting the amount of the antigen (i.e. human cytochrome P450).

The concentration of cytochrome P450 for diagnosis of hepatitis C and alcoholic cirrhosis was determined by measuring absorbance of the well at a substrate-specific wave length (492 nm) with a spectrophotometer such as a microplate-reader for 96-well micro titer plate or the like.

Figure 1A:
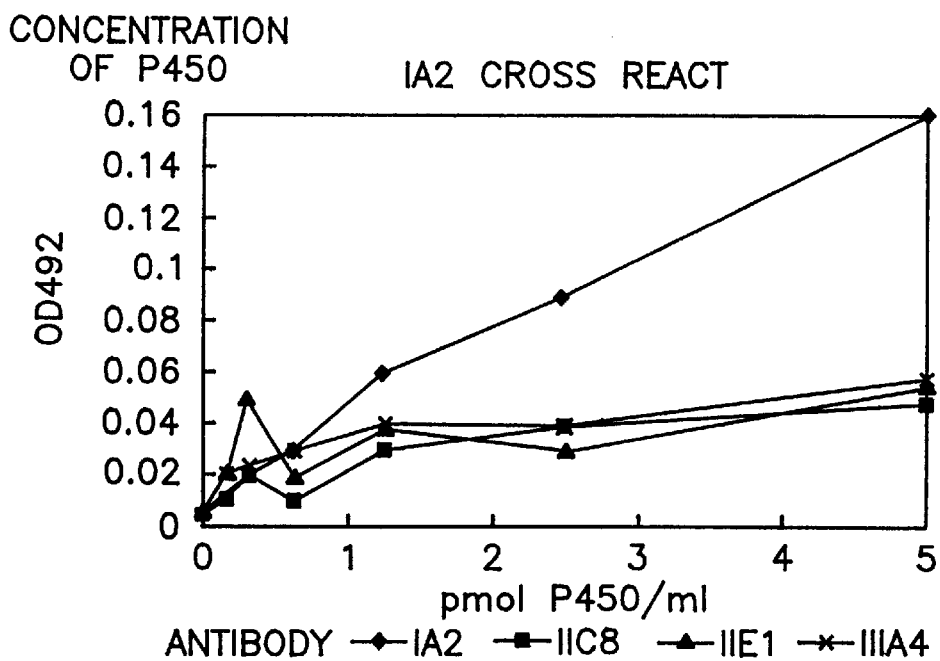
FIGS. 1A, 1B, 1C, and 1D shows the calibration curve of the concentration of cytochrome P450 obtained by using the standard human cytochrome P450 solutions as the sample and the diagnostic kit of the present invention.
Figure 1B:
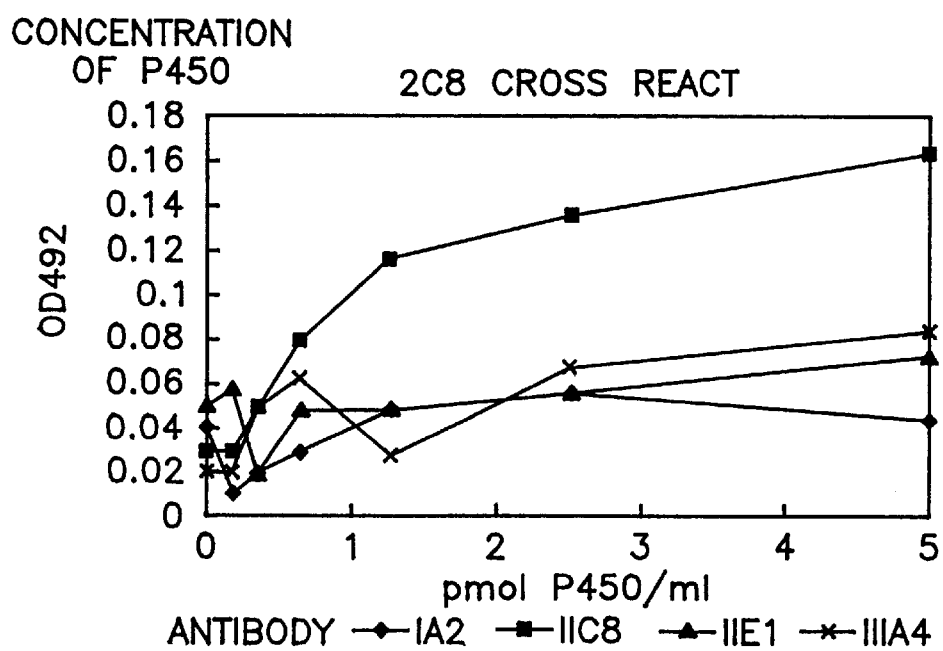
Figure 1C:
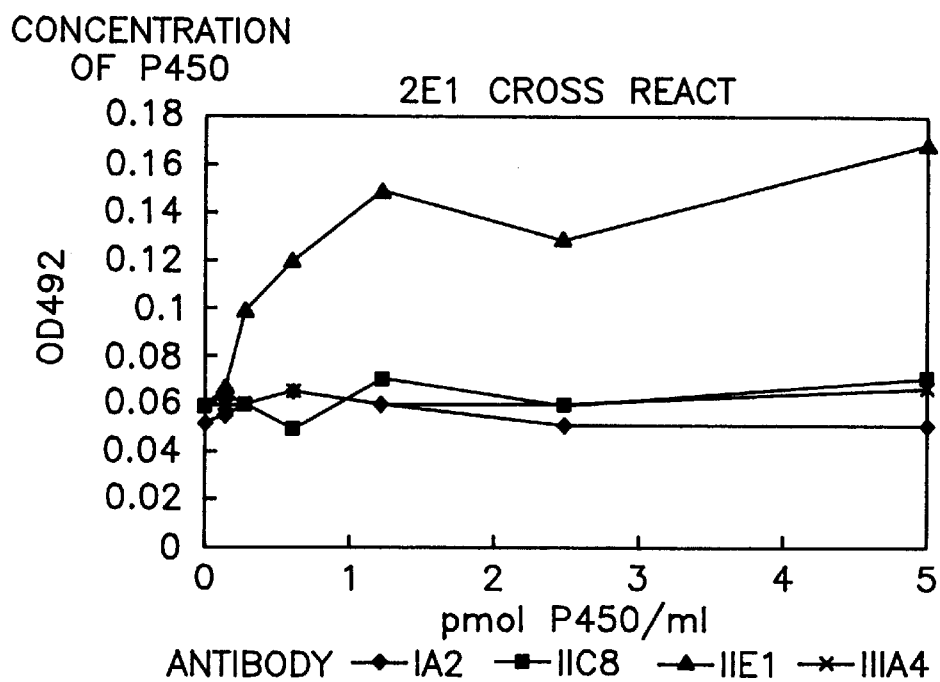
Figure 1D:
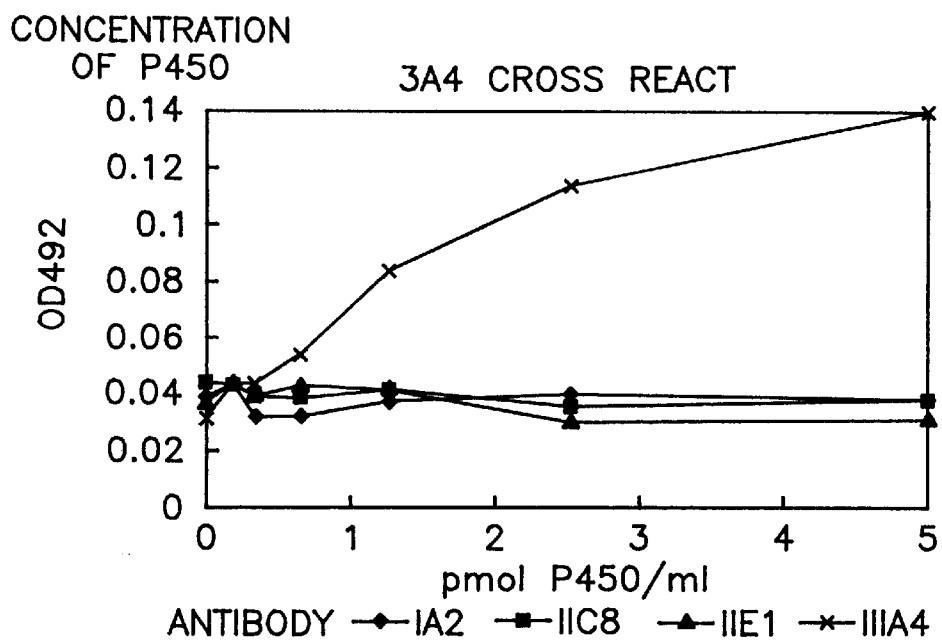

The results are shown in FIG. 1.

Test Example 2
Determination of the Concentration of a Cytochrome P450 in Human Serum for Diagnosis of Hepatitis C and Alcoholic Cirrhosis (part 2)

To a solid support obtained in Preparation Example 3 was added 100 µl per well of a human serum as the sample (obtained as a supernatant formed by centrifuging 1 ml of withdrawn blood as the sample at 4° C. and 2,000 G for 15 minutes to remove precipitates) and allowed to stand at room temperature for 1 hour to effect antigen-antibody reaction.

Next, the reaction product was treated with 100 µl of a solution of a labeled antibody prepared in Preparation Example 3 by diluting a biotin-labeled antibody (the second antibody) capable of recognizing human cytochrome P450 500 times with 10 mM phosphate buffer (pH=7.4) containing 140 mM sodium chloride and 0.1% Tween 20 and allowed to stand at room temperature for 1 hour to effect antigen-antibody reaction.

Then, wells were washed three times with about 200 µl of 10 mM phosphate buffer (pH=7.4) containing 140 mM sodium chloride and 0.1% Tween 20 in order to remove the excess labeled antibody (the second antibody) capable of recognizing human cytochrome P450.

Next, the reaction product was treated with 100 µl of streptavidin-labeled horse-radish peroxidase (HRP, for example, commercially available from Amersham), allowed to stand at room temperature for 30 minutes, washed in a similar manner as described above, treated with a substrate solution (4 mM o-phenylenediamine, 0.004% hydrogen peroxide, 0.02 M citrate, 0.05 M $Na_2HPO_4$/pH 5.0) and allowed to stand at room temperature for 30 minutes to develop brown color reflecting the amount of the antigen (i.e. human cytochrome P450).

The concentration of cytochrome P450 in human serum for diagnosis of hepatitis C and alcoholic cirrhosis was determined by measuring absorbance of the well at a substrate-specific wave length (492 nm) with a spectrophotometer such as a microplate-reader for 96-well micro titer plate or the like. The results are shown in FIG. 2.

What is claimed:

1. A method for diagnosing hepatitis C infection and alcoholic cirrhosis which comprises:

(a) conducting an antigen-antibody reaction by adding a human serum sample to a solid support to which an antibody that recognizes a human cytochrome P450 subfamily selected from the group consisting of 1A1, 1A2, 2C8, 2C9, 2C18, 2E1 and 3A4 is bound followed by removal of excess human cytochrome P450 and unreacted material by washing, (b) conducting an antigen-antibody reaction by adding a labeled antibody that recognizes a human cytochrome P450 to the reaction product followed by removal of excess labeled antibody capable of recognizing a human cytochrome P450 by washing, and (c) then detecting said cytochrome P450 by means of the label on said labeled antibody in the reaction product, wherein said cytochrome P450 is present in an amount of at least 1.25 pmol/ml in the serum.

2. The method according to claim 1, wherein the antibody that recognizes a human cytochrome P450 subfamily is an antibody which has a cross-reactivity of less than one-fourth to other cytochrome P450 subfamilies.

3. The method according to claim 2, wherein said antibody has a cross-reactivity of less than one-twentieth to other cytochrome P450 subfamilies.

4. The method according to claim 3, wherein said antibody has a cross-reactivity of less than one-hundredth to other cytochrome P450 subfamilies.

5. The process according to claim 1, wherein said cytochrome P450 is present in an amount of at least 2.5 pmol/ml in the serum.

6. The process according to claim 5, wherein said cytochrome P450 is present in an amount of at least 5 pmol/ml in the serum.

* * * * *